US008846116B2

(12) United States Patent
Koenig et al.

(10) Patent No.: US 8,846,116 B2
(45) Date of Patent: Sep. 30, 2014

(54) WIPE AND METHODS FOR IMPROVING SKIN HEALTH

(75) Inventors: David W. Koenig, Menasha, WI (US); Beth A. Lange, Germantown, TN (US); Christine L. Schneider, Pewaukee, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 851 days.

(21) Appl. No.: 11/176,060

(22) Filed: Jul. 7, 2005

(65) Prior Publication Data

US 2006/0008514 A1    Jan. 12, 2006

Related U.S. Application Data

(63) Continuation of application No. 10/624,186, filed on Jul. 22, 2003, now abandoned.

(51) Int. Cl.
| | |
|---|---|
| *A61K 36/71* | (2006.01) |
| *A61K 36/87* | (2006.01) |
| *A61K 36/00* | (2006.01) |
| *A61Q 19/00* | (2006.01) |
| *A61K 8/97* | (2006.01) |
| *A61K 8/02* | (2006.01) |
| *A61L 15/40* | (2006.01) |
| *A61F 13/84* | (2006.01) |
| *A61Q 17/00* | (2006.01) |

(52) U.S. Cl.
CPC ............ *A61K 8/97* (2013.01); *A61F 13/8405* (2013.01); *A61Q 19/00* (2013.01); *A61K 8/0208* (2013.01); *A61K 2800/70* (2013.01); *A61L 15/40* (2013.01); *A61Q 17/005* (2013.01)
USPC ........... 424/726; 424/766; 424/774; 424/779; 424/443

(58) Field of Classification Search
None
See application file for complete search history.

(56) References Cited

U.S. PATENT DOCUMENTS

| | | | |
|---|---|---|---|
| 4,100,324 A | 7/1978 | Anderson et al. | |
| 4,255,337 A | 3/1981 | Kaiser et al. | |
| 4,609,547 A | 9/1986 | Garman et al. | |
| 5,043,155 A | 8/1991 | Puchalski et al. | |
| 5,141,803 A | 8/1992 | Pregozen | |
| 5,152,996 A * | 10/1992 | Corey et al. | 424/443 |
| 5,472,700 A | 12/1995 | Staetz et al. | |
| 5,512,283 A | 4/1996 | Byers et al. | |
| 5,587,358 A | 12/1996 | Sukigara et al. | |
| 5,601,833 A | 2/1997 | Ribier et al. | |
| 5,604,262 A | 2/1997 | Wood et al. | |
| 5,648,083 A | 7/1997 | Blieszner et al. | |
| 5,656,278 A | 8/1997 | Enjolras | |
| 5,723,138 A | 3/1998 | Bae et al. | |
| 5,753,246 A * | 5/1998 | Peters | 424/404 |
| 5,804,168 A | 9/1998 | Murad | |
| 5,830,916 A | 11/1998 | Hannun et al. | |
| 5,851,782 A | 12/1998 | Hannun et al. | |
| 5,888,524 A | 3/1999 | Cole | |
| 5,906,992 A | 5/1999 | Fonsny et al. | |
| 5,916,573 A | 6/1999 | Spiers et al. | |
| 5,935,596 A | 8/1999 | Crotty et al. | |
| 5,985,300 A | 11/1999 | Crotty et al. | |
| 6,028,018 A | 2/2000 | Amundson et al. | |
| 6,060,075 A | 5/2000 | Rao et al. | |
| 6,117,440 A | 9/2000 | Suh et al. | |
| 6,159,487 A | 12/2000 | Znaiden et al. | |
| 6,174,519 B1 | 1/2001 | Greene | |
| 6,203,797 B1 | 3/2001 | Perry | |
| 6,228,265 B1 | 5/2001 | Henderson | |
| 6,235,272 B1 | 5/2001 | Greene | |
| 6,235,737 B1 | 5/2001 | Styczynski et al. | |
| 6,258,355 B1 | 7/2001 | Cavaliere widow Vesely et al. | |
| 6,280,758 B1 | 8/2001 | Warren et al. | |
| 6,338,855 B1 * | 1/2002 | Albacarys et al. | 424/409 |
| 6,485,756 B1 * | 11/2002 | Aust et al. | 424/725 |
| 6,645,506 B1 * | 11/2003 | Farmer | 424/260.1 |
| 7,585,518 B2 * | 9/2009 | Koenig et al. | 424/443 |
| 2002/0022043 A1 | 2/2002 | Miller | |
| 2002/0071859 A1 | 6/2002 | Gott et al. | |
| 2002/0136755 A1 | 9/2002 | Tyrrell et al. | |
| 2003/0120228 A1 | 6/2003 | Koenig et al. | |
| 2003/0130636 A1 * | 7/2003 | Brock et al. | 604/367 |

(Continued)

FOREIGN PATENT DOCUMENTS

| | | | |
|---|---|---|---|
| AU | 199857398 B2 | 10/1998 | |
| CN | 1071844 A | 5/1993 | |

(Continued)

OTHER PUBLICATIONS

Calderone, R.A. Adhence and Receptor Relationships of *Candida albicans*, Microbiological Reviews, (1991), pp. 1-20, vol. 65:1.

(Continued)

*Primary Examiner* — Chris R Tate
*Assistant Examiner* — Deborah Davis
(74) *Attorney, Agent, or Firm* — Armstrong Teasdale LLP

(57) ABSTRACT

The present invention relates to methods and products, such as wet wipes and absorbent articles, that are capable of imparting a health benefit when used in the intended fashion. More specifically, the products described herein comprise one or more botanical compounds, which are capable of selectively controlling the balance of flora on the skin. The compounds may enhance the adherence of healthy flora to the surface of skin or mucosa, inhibit the growth of problem flora on or around the skin surface, or inhibit the adherence of problem flora to the surface of skin or mucosa, or any combination thereof.

13 Claims, No Drawings

(56) References Cited

U.S. PATENT DOCUMENTS

| | | | |
|---|---|---|---|
| 2004/0096484 A1* | 5/2004 | Tyrrell et al. | 424/443 |
| 2004/0185123 A1* | 9/2004 | Mazzio et al. | 424/730 |
| 2004/0228811 A1* | 11/2004 | Krzysik | 424/59 |
| 2006/0165644 A1* | 7/2006 | Tanaka et al. | 424/74 |

FOREIGN PATENT DOCUMENTS

| | | | |
|---|---|---|---|
| CN | 1280008 A | | 2/2002 |
| DE | 19824680 A1 | | 12/1999 |
| DE | 19824683 A1 | | 12/1999 |
| DE | 19824727 A1 | | 12/1999 |
| DE | 19827624 A1 | | 8/2002 |
| EP | 0 350275 A2 | | 1/1990 |
| EP | 0 870507 A1 | | 10/1998 |
| EP | 0 922 457 A1 | | 6/1999 |
| EP | 0 993822 A1 | | 4/2000 |
| GB | 2 363 074 A | | 12/2001 |
| JP | 59-166585 A | | 9/1984 |
| JP | 01-207339 A2 | | 8/1989 |
| JP | 03-029823 A | | 2/1991 |
| JP | 03-236311 A | | 10/1991 |
| JP | 07-228892 A | | 8/1995 |
| JP | 08-217658 A | | 8/1996 |
| JP | 08-268859 A | | 10/1996 |
| JP | 08-294395 A | | 11/1996 |
| JP | 09-110615 A | | 4/1997 |
| JP | 09-194317 A | | 7/1997 |
| JP | 09308680 A | * | 12/1997 |
| JP | 11-116417 A | | 4/1999 |
| JP | 11-130627 A | | 5/1999 |
| JP | 11-139959 A | | 5/1999 |
| JP | 1-228325 A | | 8/1999 |
| JP | 11-292710 A | | 10/1999 |
| JP | 11-332778 A | | 12/1999 |
| JP | 2000-053533 A | | 2/2000 |
| JP | 2000-053923 A | | 2/2000 |
| JP | 2000-063262 A | | 2/2000 |
| JP | 2000-070097 A | | 3/2000 |
| JP | 2000-169359 A | | 6/2000 |
| JP | 2001-009950 A | | 1/2001 |
| JP | 2001-261543 A | | 9/2001 |
| KR | 9708991 B1 | | 6/1997 |
| WO | WO 84/02845 | | 8/1984 |
| WO | WO 96/22015 A1 | | 7/1996 |
| WO | WO 97/29783 | | 8/1997 |
| WO | WO 98/03147 A1 | | 1/1998 |
| WO | WO 98/36840 A | | 8/1998 |
| WO | WO 01/00253 A1 | | 1/2001 |
| WO | WO 01/01949 A1 | | 1/2001 |
| WO | WO 01/19325 A1 | | 3/2001 |
| WO | WO 01/26617 A1 | | 4/2001 |
| WO | WO 01/76371 A1 | | 10/2001 |
| WO | WO 01/83866 A2 | | 11/2001 |
| WO | WO 2004/045574 | | 6/2004 |

OTHER PUBLICATIONS

Di Marzio et al., Effect of the Lactic Acid Bacteria *Streptococcus thermophilus* on Ceramide Levels in Human Keratinocytes In Vitro and Stratum Comeum In Vivo, Soc. Invest. Derm., (1999), pp. 98-106, vol. 113:1.

Higaki, S. et al., *Staphylococcus* species on the Skin Surface of Infant Atopic Dermatitis Patients. J.Inter.Med.Res., (1998), pp. 98.101, vol. 26.

Hostetter, M.K., Adhesions and Ligands Involved in the Interaction of *Candida spp*. With Epithelial and Endothelial Surfaces, Clinical Microbiology Reviews, (1994), pp. 29-42, vol. 7:1.

Jin, K. et al., Analysis of beta-glucocerebrosidase and Ceramidase Activities in Atopic and Aged Dry Skin, Acta.Derm.Venerol., (1994), pp. 337-340, vol. 74.

Marekov, L.N. et al., Cermides are Bound to Structural Proteins of the Human Foreskin Epidermal Cornified Cell Envelope, J.Biol.Chem., (1998), pp. 17763-17770, vol. 273:28.

Okino, N. et al., Purification and Characterization of a Novel Ceramidase from *Pseudomonas aeruginosa*, J.Biol.Chem., (1998), pp. 14388-14373, vol. 273:23.

Tronchin, G. et al., Fungal Cell Adhesion Molecules in *Candida albicans*, European Journal of Epidemiology, (1991), pp. 23-33, vol. 7:1.

Invitation to Pay Additional Fees from PCT/US2004/011052 dated Nov. 2, 2004.

Printout from http://en.wikipedia.org/wiki/Red_alga, last modified Jan. 20, 2009, printed Jan. 22, 2009.

Printout from http://viable-herbal.com/singles/Herbs/s759.htm, printed Jan. 22, 2009.

Printout from http://en.wikipedia.org/wiki/Dilisk, last modified Dec. 24, 2008, printed Feb. 12, 2009.

Printout from http://en.wikipedia.org/w/index.php?title=Parsley&printable=yes, last modified Feb. 11, 2009, printed Feb. 13, 2009.

Translation of Notice of Preliminary Rejection received in Korean Patent Application No. 10-2006-7002750, mailed Dec. 21, 2010.

European Communication issued in Application No. 04749954.6, dated Feb. 28, 2011.

* cited by examiner

WIPE AND METHODS FOR IMPROVING SKIN HEALTH

CROSS-REFERENCE TO RELATED APPLICATIONS

This application is a continuation of U.S. application Ser. No. 10/624,186, filed Jul. 22, 2003 now abandoned, which is herein incorporated by reference in its entirety.

BACKGROUND OF THE INVENTION

The present invention relates to personal care products, such as wipes and absorbent articles, that are capable of providing a skin health benefit to the user. More particularly, the present invention relates to wet wipes comprising at least one botanical compound that selectively controls the growth and/or adherence of flora on the skin. The botanical compounds described herein and suitable for incorporation into a wipe or absorbent article may selectively promote the adherence of healthy flora to the surface of skin or mucosa, selectively inhibit the growth of problem flora on or around the skin surface, selectively inhibit the adherence of problem flora to the surface of skin or mucosa, or provide multiple combinations of these effects.

A variety of flora, both beneficial and pathogenic, may be found on the skin at any given time. Problem flora, such as pathogenic bacteria and yeast, have been associated with numerous ailments, including skin infections, diaper rash, urinary or vaginal infections, and malodors, and are associated with various irritants, such as proteases, lipases, carbohydrases, lipopolysaccharides ("LPS"), volatile organic compounds ("VOCs"), and other bio-molecules. In contrast, healthy bacteria attach to the skin, and may provide a variety of benefits, including playing a role in preventing pathogenic organisms from colonizing or growing.

The disruption in the protection of healthy flora may result in the colonization of other organisms, which in turn may cause irritation, infection, and diseases on or near the skin surface. One example of a healthy bacterium is *Lactobacillus acidophilius*, which colonizes the vaginal epithelium during child-bearing years, and inhibits the growth of pathogens. Another skin bacterium which can have positive health attributes is *Staphylococcus epidermidis*. *S. epidermidis* is a normal microbial inhabitant of human skin. In most cases, strains of *S. epidermidis* are nonpathogenic and play a protective role in their host. For instance, *S. epidermidis* appears to prevent colonization of the skin by dermatophytic fungi, and may alter the production of irritating metabolites. In limited circumstances, *S. epidermidis*, however, can become an opportunistic pathogen by spreading into the blood through breaks in skin barriers. Individuals most susceptible to *S. epidermidis* infection are intravenous drug users, newborns, elderly, and those using catheters or other artificial appliances. Regardless, *S. epidermidis* is generallly regarded as a bacteria that provides a health benefit.

In contrast, an example of a common pathogenic flora is *Candida albicans*. When in yeast form, *C. albicans* naturally inhabits the human digestive tract, and is a normal part of bowel flora. However, under certain conditions, such as a weakened immune system, a high sugar diet, or improper pH in the digestive system, among others, *C. albicans* may shift from the yeast stage, to an invasive mycelial fungal form. The mycelial fungal form of *C. albicans* binds readily to the skin and mucus membranes, and is associated with a wide variety of infections, including vaginal yeast infections, oral infections, and diaper rash.

Other common pathogenic flora include *Pseudomonas aeruginosa, Proteus mirabilis,* and *Escherichia coli.* Like *C. albicans, E. coli* naturally inhabit the human gastro-intestinal tract. However, *E. coli* can be pathogenic, and are responsible for several types of infections in humans, including urinary tract infections. For example, *E. coli* can colonize from the feces or perineal region, and ascend the urinary tract to the bladder, causing infection and irritation.

*P. aeruginosa* is an opportunistic pathogen of humans, and is resistant to many antibiotics. *P. aeruginosa* may infect almost any type of compromised tissue, and can cause a variety of infections, including urinary tract infections, respiratory system infections, dermatitis, soft tissue infections, and bacteremia, as well as a variety of systemic infections, particularly in immunosuppressed patients.

*P. mirabilis* is a Gram negativie rod that is widely distributed in nature and easily isolated in the feces of most animals, but is hardly ever found in high numbers unless the normal intestinal microflora is altered. *P. mirabilis* can cause invasive diarrhea and severe infections of the upper urinary tract, and has also been implicated in infections of blood and wounds.

To date, skin cleaning products, such as wet wipes and dry wipes, have primarily cleaned the skin by attempting to remove and/or kill all flora present on the skin, regardless of whether the flora are potentially beneficial or potentially harmful. For example, numerous commercially available wet wipes comprise at least one antimicrobial compound, such as an organic acid, which is typically used in combination with a surfactant to kill flora on the skin surface. Although typically effective in killing flora located on the skin surface, the antimicrobial wipe kills all flora and does not, and cannot, distinguish between "good" and "bad" flora.

Based on the foregoing, it would be desirable to provide a skin health benefit for inhibiting the growth or adherence to the skin of problem flora, while maintaining, or even enhancing the adherence of healthy flora. Products, such as wipes or absorbent articles, that comprise one or more compounds capable of selectively controlling the growth and/or adherence of flora to the skin would thus be desirable, and could impart a beneficial health effect to the user.

SUMMARY OF THE INVENTION

The present invention relates to products and methods for selectively controlling the balance of flora on the skin. More specifically, the present invention relates to products such as wet wipes or absorbent articles containing one or more botanical compounds that promote the adherence of healthy flora to the surface of skin or mucosa, inhibit the growth of problem flora on or around the skin surface, inhibit the adherence of problem flora to the surface of skin or mucosa, or any combination thereof.

Briefly, in one embodiment, the present invention is directed to a product for promoting the adherence of *Lactobacillus acidophilus* to the surface of skin or mucosa. The product comprises a substrate and a botanical compound that is capable of increasing the adherence of *Lactobacillus acidophilus* by at least about 50%, as defined herein.

In another embodiment, the present invention is directed to a product for promoting the adherence of *Staphlococcus epidermidis* to the surface of skin. The product comprises a substrate and a botanical compound that is capable of increasing the adherence of *Staphlococcus epidermidis* by at least about 50%, as defined herein.

The present invention also relates to products, such as wipes or absorbent aritcles, for inhibiting the adherence of problem organisms to the surface of skin or mucosa. The product comrises a substrate, such as a fibrous wipe substrate or an absorbent substrate, and a botanical compound that is capable of inhibiting the adherence of a problem organism by at least about 50%, as defined herein. The problem organism may be *Candida albicans, Proteus mirabilis, Pseudomonas aeruginosa, Staphlococcus epidermidis*, or a combination thereof.

The present invention is also directed to a product for inhibiting growth of one or more bacteria or yeast on or around the skin's surface. The product comprises a botanical compound suitable for inhibiting the growth of *Candida albicans, Proteus mirabilis, Pseudomonas aeruginosa*, and/or *Staphlococcus epidermidis*.

Furthermore, the present invention relates to products comprising a substrate, such as a fibrous wipe substrate or absorbent substrate, and a combination of two or more botanical compounds that may provide differing beneficial effects. In one embodiment, the product comprises a first botanical compound that promotes the adherence of *Lactobacillus acidophilus* to the surface of skin or mucosa by at least about 50%, and a second botanical compound that inhibits the adherence of at least one organism to the surface of skin or mucosa by at least about 50%, the organism selected from the group consisting of *Candida albicans, Proteus mirabilis, Pseudomonas aeruginosa*, and *Staphylococcus epidermidis*.

In another embodiment, the product comprises a first botanical compound that promotes the adherence of *Lactobacillus acidophilus* to the surface of skin or mucosa by at least about 50%, and a second botanical compound that promotes the adherence of *Staphylococcus epidermidis* to the surface of skin by at least about 50%.

In yet another embodiment, the product comprises a first botanical compound that inhibits the adherence of at least one organism to the surface of skin or mucosa by at least about 50%, the organism selected from the group consisting of *Candida albicans, Proteus mirabilis, Pseudomonas aeruginosa*, and *Staphylococcus epidermidis*, and a second botanical compound that inhibits the growth of at least one organism on or around the skin surface, the organism selected from the group consisting of *Candida albicans, Proteus mirabilis, Pseudomonas aeruginosa*, and *Staphylococcus epidermidis*, wherein the second botanical compound has an IC50 value of about 5% or less for *Candida albicans, Proteus mirabilis, Pseudomonas aeruginosa*, or *Staphylococcus epidermidis*.

The present invention also relates to a method for promoting the adherence of *Lactobacillus acidophilus* to the surface of skin or mucosa, and to a wet wipe for promoting the adherence of *Lactobacillus acidophilus* to the surface of skin or mucosa.

DETAILED DESCRIPTION OF THE PREFERRED EMBODIMENTS

In accordance with the present invention, it has been discovered that certain bio-compounds, such as specific botanical extracts or botanical actives, can be utilized in combination with personal care products, such as wipes or absorbent articles, to impart a skin health benefit by selectively controlling the balance of flora on the skin. More specifically, it has been discovered that certain botanical compounds may provide at least one of the following benefits when used in combination with a wipe substrate or absorbent article and contacted with the skin or mucosa: (i) promote the adherence of healthy flora to the surface of skin or mucosa, (ii) inhibit the growth of problem flora on the skin surface, and/or (iii) inhibit the adherence of problem flora to the surface of skin or mucosa. By introducing a botanical compound, or a combination of botanical compounds having one or more of these characteristics into a solution that is used in combination with a wipe or absorbent article substrate, it is possible to selectively control the growth and adherence of various bacteria and yeast on the skin.

The personal care products of the present invention contain at least one botanical compound. As used herein, the term "botanical compound" is meant to include bio-compounds such as botanical extracts and/or botanical actives, as well as essential oils and herbs. The botanical compound is capable of improving the health of skin contacted by the wipe or absorbent article during normal use by selectively controlling the growth and/or adherence of flora to the skin. Numerous personal care products can be used in combination with the botanical compounds described herein in accordance with the present invention to impart a skin health benefit to the user. For example, one or more of the botanical compounds described herein can be used in combination with wipes, such as wet wipes, hand wipes, face wipes, cosmetic wipes, household wipes, dry wipes, feminine wipes, and the like, to selectively control the balance of flora on the skin by reducing the growth or adherence of problem flora, such as pathogenic bacteria or yeast, to the skin, and/or promoting the adherence of beneficial flora, such as healthy bacteria, to the surface of skin or mucosa.

In addition, one or more of the botanical compounds described herein can be used in combination with an absorbent article such as diapers, training pants, adult incontinence garments, feminine napkins, tampons, interlabial pads, facial tissue, wound management products, paper towels, and bath tissue. As will be understood by one skilled in the art, the botanical compound may be directly impregnated on the wipe or absorbent substrate, or may be in a liquid formulation or ointment used with the wipe or absorbent article.

Although discussed primarily in combination with a wipe substrate, it should be understood that the botanical compounds can also be used in combination with other nuerous absorbent products described above. Materials suitable for use as the substrate of the wipe are well known to those skilled in the art, and typically include a fibrous sheet material, which may be either woven or nonwoven. For example, the wipes incorporating the botanical compounds described herein to improve skin health may include nonwoven fibrous sheet materials, which include meltblown, coform, air-laid, bonded-carded web materials, hydroentangled materials, and combinations thereof. Such materials can be comprised of synthetic or natural fibers, or a combination thereof. Typically, wipes define a basis weight of from about 25 to about 120 grams per square meter and desirably from about 40 to about 90 grams per square meter.

In a particular embodiment, the wipes incorporating the botanical compounds described herein comprise a coform basesheet of polymeric microfibers and cellulosic fibers having a basis weight of from about 60 to about 80 grams per square meter and desirably about 75 grams per square meter. Such coform basesheets are manufactured generally as described in U.S. Pat. No. 4,100,324, which is incorporated by reference. Typically, such coform basesheets comprise a gas-formed matrix of thermoplastic polymeric meltblown microfibers, such as, for example, polypropylene microfibers, and cellulosic fibers, such as, for example, wood pulp fibers.

The relative percentages of the polymeric microfibers and cellulosic fibers in the coform basesheet can vary over a wide range depending upon the desired characteristics of the wet wipes. For example, the coform basesheet may comprise from about 20 to about 100 weight percent, desirably from about 20 to about 60 weight percent, and more desirably from about 30 to about 40 weight percent of the polymeric microfibers based on the dry weight of the coform basesheet being used to provide the wipes.

Alternatively, the wipes incorporating the botanical compounds described herein can comprise a composite, which includes multiple layers of materials such as those described in U.S. Pat. No. 6,028,018, which is incorporated by reference. For example, the wipes may include a three layer composite, which includes an elastomeric film or meltblown layer between two coform layers as described above. In such a configuration, the coform layers may define a basis weight of from about 15 to about 30 grams per square meter and the elastomeric layer may include a film material such as a polyethylene metallocene film.

As mentioned above, one type of wipe suitable for use in combination with the botanical compounds described herein to improve skin health include wet wipes, which, in addition to the wipe substrate, comprise a liquid solution or formulation. The liquid solution or formulation can be any liquid, which can be absorbed into the wet wipe basesheet and may include any suitable components, which provide the desired wiping properties. For example, the components may include water, emollients, surfactants, fragrances, preservatives, chelating agents, pH buffers, or combinations thereof as are well known to those skilled in the art. Further, the liquid may also contain lotions, medicaments, and/or antimicrobials.

The amount of liquid contained within each wet wipe may vary depending upon the type of material being used to provide the wet wipe, the type of liquid being used, the type of container being used to store the wet wipes, and the desired end use of the wet wipe. Generally, each wet wipe can contain from about 150 to about 600 weight percent and desirably from about 250 to about 450 weight percent liquid based on the dry weight of the wipe for improved wiping. In a particular aspect, the amount of liquid contained within the wet wipe is from about 300 to about 400 weight percent and desirably about 330 weight percent based on the dry weight of the wet wipe. If the amount of liquid is less than the above-identified ranges, the wet wipe may be too dry and may not adequately perform. If the amount of liquid is greater than the above-identified ranges, the wet wipe may be oversaturated and soggy and the liquid may pool in the bottom of the container.

Each wet wipe is generally rectangular in shape and may have any suitable unfolded width and length. For example, the wet wipe may have an unfolded length of from about 2.0 to about 80.0 centimeters and desirably from about 10.0 to about 25.0 centimeters and an unfolded width of from about 2.0 to about 80.0 centimeters and desirably from about 10.0 to about 25.0 centimeters. Typically, each individual wet wipe is arranged in a folded configuration and stacked one on top of the other to provide a stack of wet wipes. Such folded configurations are well known to those skilled in the art and include c-folded, z-folded, quarter-folded configurations and the like. The stack of folded wet wipes may be placed in the interior of a container, such as a plastic tub, to provide a package of wet wipes for eventual sale to the consumer. Alternatively, the wet wipes may include a continuous strip of material which has perforations between each wipe and which may be arranged in a stack or wound into a roll for dispensing.

In one embodiment of the present invention, one or more botanical compounds are introduced into or onto a fibrous wipe substrate, absorbent substrate, a solution or ointment for use with a wipe substrate or absorbent article. When the wipe or absorbent article contacts skin or mucosa, the botanical compound contacts the skin or mucosa, and may be actually transferred to the skin or mucosa, thereby selectively affecting the growth and/or adherence of flora to the portion of the skin or mucosa contacted by the wipe or absorbent article. In a specific embodiment, the botanical compound is introduced into the liquid formulation of a wet wipe. The botanical compound preferably promotes the adherence of at least one healthy flora to the surface of skin or mucosa, and/or inhibits the growth of at least one problem flora on or around the skin surface, and/or inhibits the adherence of at least one problem flora to the surface of skin or mucosa.

As noted above, beneficial flora are often naturally found on the skin or mucosal surfaces of the body, and may provide a variety of beneficial effects. It is thus often desirable to maintain or promote the adherence of such healthy flora to the surface of skin or mucosa to increase the benefit. Some examples of healthy flora include *Lactobacillus acidophilus*, some other *Lactobacillus species*, and *Atopobium species*, and to an extent, *Staphlococcus epidermidis*.

Unlike healthy flora, problem flora, such as pathogenic bacteria or yeast, as noted above, are associated with numerous ailments, including skin infections, diaper rash, urinary or vaginal infections, and malodors, among others. As such, it is often desirable to selectively inhibit the growth and/or adherence of these problem flora. Some examples of problem flora include *Candida albicans, Proteus mirabilis*, and *Pseudomonas aeruginosa*. It will be apparent to those skilled in the art that there are numerous other examples of both healthy and problem flora, other than those described herein, and that the growth and/or adherence of these flora may be controlled in a manner similar to that described herein.

Suitable botanical compounds for use in combination with the personal care products described herein include botanical compounds that have one or more of the following effects when contacted with the skin: (i) promote the adherence of *Lactobacillus acidophilus* to the surface of skin or mucosa; (ii) promote the adherence of *Staphlococcus epidermidis* to the surface of skin; (iii) inhibit the growth on or around the skin surface of at least one organism selected from the group consisting of *Candida albicans, Proteus mirabilis, Pseudomonas aeruginosa*, and *Staphlococcus epidermidis*; and (iv) inhibit the adherence to the surface of skin or mucosa of at least one organism selected from the group consisting of *Candida albicans, Proteus mirabilis, Pseudomonas aeruginosa*, and *Staphlococcus epidermidis*.

The protocols for testing the ability of botanical compounds to elicit any of these desired effects are set forth in the Examples. In general, the ability of a botanical compound to affect the adherence of an organism to skin is determined by comparing the adherence of the organism to skin in the presence of the botanical compound, to the adherence of the organism to skin in the absence of the botanical compound. If the amount of adherence in the presence of the botanical compound is 150% or greater than the amount of adherence in the absence of the botanical compound, then the botanical compound is an adherence promoter for that organism. If the amount of adherence in the presence of the botanical compound is 50% or less than the amount of adherence in the absence of the botanical compound, then the botanical compound is an anti-adherent for that organism.

Similarly, the ability of a compound to inhibit the growth of an organism (Examples 1 and 2) is determined relative to a control. As the following equations indicate, optical density of a sample containing a botanical compound and an organism and a control containing only the organism are measured at 0 and 18 hours:

$$[(OD_{650} \text{ sample @18 hours} - OD_{650} \text{ sample @0 hours})/(OD_{650} \text{ yeast only @18 hours} - OD_{650} \text{ yeast only @0 hours})]*100;$$

[($OD_{650}$ sample @18 hours−$OD_{650}$ sample @0 hours)/($OD_{650}$ bacteria only @18 hours−$OD_{650}$ bacteria only @0 hours)]*100.

For purposes of the present invention, a botanical compound is considered a growth inhibitor if the botanical compound has an IC50 value of 5% or less for the organism being tested, wherein IC50 is the concentration that inhibits the growth of the organism by 50%.

A variety of botanical compounds were tested using the protocols described herein with the results set forth in Tables 1 and 2. However, the ability of numerous other botanical compounds to affect the growth and/or adherence of healthy and/or problem flora to the surface of skin or mucosa, in addition to those tested herein, may also be determined using these protocols.

Some botanical compounds may have multiple beneficial effects. In addition, some botanical compounds may have one or more beneficial effect, as described above, as well as a less desired effect, such as inhibiting the adherence of *Lactobacillus acidophilus* to the surface of skin or mucosa. Such compounds may still be useful in combination with a wipe or absorbent article, of the present invention, depending on the type of wipe or absorbent article and the intended use of such product.

In one specific embodiment, a botanical compound which does not substantially promote the adherence of *C. albicans, P. mirabilis*, and *P. aeruginosa* is introduced into a solution for use in combination with a wipe substrate or absorbent article. In this embodiment, the botanical compound may increase the adherence of *L. acidophilus* or *S. epidermidis*, or may inhibit the growth and/or adherence to the surface of skin or mucosa of *S. epidermidis, C. albicans, P. mirabilis*, or *P. aeruginosa*. Suitable botanical compounds include Aloe Ferox HS, American Ginseng, Arkin Special, Bleuet MCF 783 Hydro, Calendula (Marigold), Ceramide Complex, Comfey leaves, Cromoist 0-25, Cromoist HYA, Dandelion, Devil's Claw, Dong Quai, Drago-Oat Active, Echinacea Dry Aq., Gingko Biloba, Ginseng GR 471 Hydro, Glucosamine 99, Goldenseal, Gotu Kola PG 5:1, Grape Seed, Grape Seed Extr., Green Tea, Green Tea Conc., Green Tea Extr., Green Tea HS, Hydrocotyle GR 040, Hydrolactin 2500, Hydrolite-5, Hydrosoy 2000 SF, Lamier Blanc MCF 796, Lavendar MCF 1484, Lime Blossom, Lime Blossom Distillate, Marigold (Calendula), Marron d'inde (horse chestnut), Marron d'inde MCF 1972, Milk Thistle, Nab Willowbark Extr., NSLE Lipomicron, Pineapple B, Sage Special, Sandal Complex, Soluble Wheat Protein, Spirulina, St. John's Wort W/S, White Mistle Toe, Witchhazel distillate, Witchhazel GW, Yucca 70, and. Yucca Extr. Powder 50%.

As previously discussed, *L. acidophilus* is a beneficial organism. As such, it is desirable to promote the adherence of *L. acidophilus* to the surface of skin or mucosa. Thus, in one embodiment, a botanical compound that is capable of increasing the adherence of *L. acidophilus* to the surface of skin or mucosa by at least about 50%, is incorportaed into or onto a product of the present invention. Suitable botanical compounds include Aloe Ferox HS, American Ginseng, Calendula (Marigold), Ceramide Complex, Comfey Leaves, Cromoist 0-25, Cromoist HYA, Dandelion, Devil's Claw, Dong Quai, Drago-Oat Active, Echinacea Dry Aq., Gingko Biloba, Ginseng GR 471 Hydro, Glucosamine 99, Goldenseal, Gotu Kola PG 5:1, Grape Seed, Green Tea, Hydrolite-5, Hydrosoy 2000 SF, Marron D'Inde (Horse Chestnut), Milk Thistle, Nab Willowbark Extr., Soluble Wheat Protein, Spirulina, St. John's Wort W/S, White Mistle Toe, Witchhazel Distillate, Witchhazel GW, Yucca 70, and Yucca Extr. Powder 50%. More specifically, the botanical compound is capable of increasing the adherence of *L. acidophilus* to the surface of skin or mucosa by at least about 1000%. Suitable botanical compounds include Calendula (Marigold), Ceramide Complex, Echinacea Dry Aq., Grape Seed, Spirulina, Witchhazel GW, and Yucca 70. Additionally, a suitable botanical compound that is capable of increasing the adherence of *L. acidophilus* to the surface of skin or mucosa is selected from the group consisting of Aloe Ferox HS, American Ginseng, Calendula (Marigold), Ceramide Complex, Comfey Leaves, Cromoist 0-25, Cromoist HYA, Dandelion, Devil's Claw, Dong Quai, Drago-Oat Active, Ginseng GR 471 Hydro, Glucosamine 99, Gotu Kola PG 5:1, Grape Seed, Hydrolite-5, Hydrosoy 2000 SF, Marron D'Inde (Horse Chestnut), Milk Thistle, Soluble Wheat Protein, Spirulina, Witchhazel Distillate, and Witchhazel GW.

The product comprising the botanical compound that promotes the adherence of *L. acidophilius* to the skin can be a feminine wipe, feminine napkin, tampon, or interlabial pad. A feminine wipe is a hygenic wipe that may be used to clean blood, menses and/or other body exudates from the skin and hair in the pudendal region of the body. As previously discussed, *L. acidophilius* colonizes the vaginal epithelium during child-bearing years, and inhibits the growth of some pathogens in the vaginal region. It would thus be particularly beneficial to introduce into or onto a feminine product one or more botanical compounds that promote the adherence of *L. acidophilius* to the surface of skin or mucosa. In contrast, botanical compounds such as Grape Seed Extract, Green Tea Conc., Lavendar MCF 1484, Lime Blossom, Lime Blossom Distillate, and Pineapple B inhibit the adherence of *L. acidophilius* to the surface of skin or mucosa, and would thus not be particularly beneficial for a feminine product, but may be suitable for use in combination with other types of wipes or absorbent articles, as described herein.

As previously indicated, in some instances it may be beneficial to promote the adherence of *S. epidermidis* to the surface of skin. Thus, a botanical compound that is capable of promoting the adherence of *S. epidermidis* to the surface of skin by at least about 50% can be used in combination with a product of the present invention. Suitable botanical compounds include Bleuet MCF 783 Hydro, Hydrocotyle GR 040, Hydrolactin 2500, Lavendar MCF 1484, Lime Blossom, Lime Blossom Distillate, Marigold (Calendula), and Sage Special.

As previously discussed, *L. acidophilius* is a beneficial flora, and, as such, it is advantageous not to inhibit the growth or adherence of *L. acidophilius* to the surface of skin or mucosa. Thus, in an even more specific embodiment of the above, the botanical compound is capable of increasing the adherence of *S. epidermidis* to the surface of skin by at least about 50%, and does not inhibit the growth of *L. acidophilius* on or around the skin surface, nor does it significantly inhibit the adherence of *L. acidophilius* to the surface of skin or mucosa. Such suitable botanical compounds include Bleuet MCF 783 Hydro, Hydrocotyle GR 040, Hydrolactin 2500, Marigold (Calendula), and Sage Special.

In addition to promoting the adherence of healthy flora, it may be beneficial to inhibit the adherence of problem flora to the surface of skin or mucosa. The products of the present invention may thus incorporate a botanical compound that inhibits the adherence of *C. albicans, P. mirabilis*, or *P. aeruginosa* to the surface of skin or mucosa. Thus, in one embodiment, the botanical compound is capable of inhibiting the adherence of *C. albicans* to the surface of skin or mucosa by at least about 50%. Suitable botanical compounds include Aloe Ferox HS, American Ginseng, Arkin Special, Comfey Leaves, Dong Quai, Echinacea Dry Aq., Glucosamine 99, Goldenseal, Grape Seed, Grape Seed Extr., Green Tea, Green Tea Conc., Green Tea Extr., Green Tea HS, Hydrolite-5, Lavendar MCF 1484, Marron D'Inde MCF 1972, Marron D'Inde (Horse Chestnut), Pineapple B, Sandal Complex, Soluble Wheat Protein, Yucca 70, and Yucca Extr. Powder 50%. More specifically, the botanical compound is capable of inhibiting the adherence of *C. albicans* to the surface of skin or mucosa by at least about 70%. Suitable botanical compounds include Aloe Ferox HS, Comfey Leaves, Glucosamine 99, Grape Seed, Green Tea, Green Tea Extr., Hydrolite-5, Pineapple B, Sandal Complex, Yucca 70, and Yucca Extr. Powder 50%. The botanical compound capable of inhibiting the adherence of *C. albicans* may also be selected from the group consisting of Aloe Ferox HS, American Ginseng, Comfey Leaves, Dong Quai, Glucosamine 99, Grape Seed, Green Tea Conc., Hydrolite-5, Lavendar MCF 1484, Marron D'Inde MCF 1972, Marron D'Inde (Horse Chestnut), Pineapple B, Sandal Complex, and Soluble Wheat Protein.

In another specific embodiment, the botanical compound is capable of inhibiting the adherence of *P. mirabilis* to the surface of skin or mucosa by at least about 50%. Suitable botanical compounds include Aloe Ferox HS, Cromoist HYA, Echinacea Dry Aq., Gingko Biloba, Grape Seed Extr., Green Tea, Green Tea Extr., Green Tea HS, Hydrolactin 2500, Hydrolite-5, Hydrosoy 2000 SF, Marron D'Inde (Horse Chestnut), Marron D'Inde MCF 1972, NSLE Lipomicron, Pineapple B, Sandal Complex, Witchhazel GW, Yucca 70, and Yucca Exr. Powder 50%. More specifically, the botanical compound is capable of inhibiting the adherence of *P. mirabilis* to the surface of skin or mucosa by at least about 70%. Suitable botanical compounds include Aloe Ferox HS, Echinacea Dry Aq., Gingko Biloba, Grape Seed Extr., Green Tea, Green Tea Extr., Hydrolactin 2500, Hydrolite-5, Marron D'Inde (Horse Chestnut), NSLE Lipomicron, Pineapple B, Sandal Complex, Witchhazel GW, Yucca 70, and Yucca Extr. Powder 50%. Even more specifically, the botanical compound capable of inhibiting the adherence of *P. mirabilis* is selected from the group consisting of Aloe Ferox HS, Hydrolactin 2500, Hydrolite-5, Marron D'Inde (Horse Chestnut), Pineapple B, Sandal Complex, and Witchhazel GW.

In another specific embodiment, the botanical compound is capable of inhibiting the adherence of *Pseudomonas aeruginosa* to the surface of skin or mucosa by at least about 50%. Suitable botanical compounds include Ceramide Complex, Echinacea Dry Aq., Grape Seed Extr., Green Tea, Green Tea Extr., Hydrolite-5, Nab Willowbark Extr., NSLE Lipomicron, Pineapple B, Sandal Complex, Soluble Wheat Protein, Yucca 70, and Yucca Extr. Powder 50%. More specifically, the botanical compound capable of inhibiting the adherence of *Pseudomonas aeruginosa* is selected from the group consisting of Ceramide Complex, Hydrolite-5, NSLE Lipomicron, Pineapple B, Sandal Complex, and Soluble Wheat Protein.

Since, as previously discussed, *S. epidermidis* can become an opportunistic pathogen, especially when exposed to breaks in the skin barrier, it would be advantageous to inhibit the adherence of *S. epidermidis* to the surface of skin, or to inhibit the growth of *S. epidermidis* on or around the skin surface when treating wounds. Thus, it would be particularly beneficial to introduce into or onto a wipe used for wound care or other wound management products a botanical compound that inhibits the adherence of *Staphlococcus epidermidis* to the surface of skin and/or inhibits the growth of *S. epidermidis* on or around the skin surface.

The products of the present invention may thus incorporate a botanical compound that inhibits the adherence of *S. epidermidis* to the surface of skin. In one embodiment, the botanical compound is capable of inhibiting the adherence of *Staphlococcus epidermidis* to the surface of skin by at least about 50%. Suitable botanical compounds include Aloe Ferox HS, Arkin Special, Comfey Leaves, Cromoist HYA, Devil's Claw, Echinacea Dry Aq., Gingko Biloba, Goldenseal, Gotu Kola PG 5:1, Grape Seed Extr., Green Tea, Hydrosoy 2000 SF, Marron D'Inde (Horse Chestnut), Marron D'Inde MCF 1972, Pineapple B, Soluble Wheat Protein, St. John's Wort W/S, White Mistle Toe, and Yucca 70. More specifically, the botanical compound that is capable of inhibiting the adherence of *Staphlococcus epidermidis* is selected from the group consisting of Aloe Ferox HS, Comfey Leaves, Cromoist HYA, Devil's Claw, Gotu Kola PG 5:1, Hydrosoy 2000 SF, Marron D'Inde (Horse Chestnut), Marron D'Inde MCF 1972, Pineapple B, and Soluble Wheat Protein.

In another embodiment, the botanical compound is capable of inhibiting the growth of *Staphlococcus epidermidis* on or around the skin surface. Suitable botanical compounds include compounds that have an IC50 value of about 5% or less for *S. epidermidis*, including Aloe Ferox HS, Goldenseal, Grape Seed Extr., Green Tea, and Pineapple B. More specifically, the botanical compound that is capable of inhibiting the growth of *Staphlococcus epidermidis* is selected from the group consisting of Aloe Ferox HS and Pineapple B.

As previously discussed, it may be beneficial to inhibit the growth of other problem flora on or around the skin surface. The products of the present invention may thus incorporate a botanical compound that inhibits the growth of *C. albicans, P. mirabilis*, or *P. aeruginosa* on or around the skin surface. Thus, in one specific embodiment, the botanical compound is capable of inhibiting the growth of *Candida albicans* on or around the skin surface. Suitable botanical compounds include compounds that have an IC50 value of about 5% or less for *C. albicans*, and include Echinacea Dry Aq., Glucosamine 99, Goldenseal, Grape Seed Extr., Green Tea, Green Tea Conc., and Green Tea Extr. More specifically, the botanical compound that is capable of inhibiting the growth of *Candida albicans* is selected from the group consisting of Glucosamine 99 and Green Tea Conc.

In another specific embodiment, the botanical compound is capable of inhibiting the growth of *Proteus mirabilis* on or around the skin surface. Suitable botanical compounds include compounds that have an IC50 value of about 5% or less for *Proteus mirabilis*, including Gingko Biloba, Grape Seed Extr., Hydrolite-5, and Yucca 70. More specifically, the botanical compound that is capable of inhibiting the growth of *Proteus mirabilis* is Hydrolite-5.

In yet another specific embodiment, the botanical compound is capable of inhibiting the growth of *Pseudomonas aeruginosa* on or around the skin surface. Suitable botanical compounds include compounds that have an IC50 value of about 5% or less for *Pseudomonas aeruginosa*, including Grape Seed Extr., Green Tea Extr., and Hydrolite-5. More specifically, the botanical compound that is capable of inhibiting the growth of *Pseudomonas aeruginosa* is Hydrolite-5.

The products of the present invention may also incorporate a botanical compound that is capable of inhibiting the growth of at least one problem flora on or around the skin surface, the problem flora selected from the group consisting of *Candida albicans, Proteus mirabilis*, and *Pseudomonas aeruginosa*. Suitable botanical compounds are selected from the group consisting of Green Tea Extr., Hydrolite-5, Sandal Complex, and Yucca Extr. Powder 50%, and more specifically, from the group consisting of Hydrolite-5 and Sandal Complex.

The products of the present invention may also comprise a combination of two or more of the botanical compounds described herein in order to provide multiple benefits to the end user. Numerous combinations of botanical compounds may be introduced onto a wipe substrate, absorbent substrate, or into a wet wipe solution for use in combination with a wipe substrate, wherein each botanical compound provides at least one different effect than any other compound. For example, one beneficial combination would be to promote the adherence of *Lactobacillus acidophilus*, while at the same time inhibiting the adherence of at least one problem organism. Thus, in one embodiment, a product of the present invention incorporates a first botanical compound that promotes the adherence of *Lactobacillus acidophilus* to the surface of skin or mucosa by at least about 50% in combination with a second botanical compound that inhibits the adherence of at least one organism to the surface of skin or mucosa, the organism selected from the group consisting of *Candida albicans, Proteus mirabilis, Pseudomonas aeruginosa*, and *Staphylococcus epidermidis*. In this embodiment, the second botanical compound is capable of inhibiting the adherence of the organism to the surface of skin or mucosa by at least about 50%.

In addition to promoting the adherence of *Lactobacillus acidophilus* and inhibiting the adherence of at least one problem organism, it may also be beneficial to inhibit the growth of one or more problem organism such as *C. albicans, P. mirabilis, P. aeruginosa*, and/or *S. epidermidis*. Thus, these products may additionally incorporate a third botanical that inhibits the growth of *C. albicans, P. mirabilis, P. aeruginosa*, and/or *S. epidermidis* on or around the skin surface. In one embodiment, the third botanical has an IC50 value of about 5% or less for *C. albicans*. In another embodiment, the third botanical has an IC50 value of about 5% or less for *P. mirabilis*. In yet another embodiment the third botanical has an IC50 value of about 5% or less for *P. aeruginosa*. In still another embodiment, the third botanical has an IC50 value of about 5% or less for *S. epidermidis*.

Another beneficial combination would be to promote the adherence of *Lactobacillus acidophilus*, while at the same time promoting the adherence of *Staphylococcus epidermidis*. Thus, in one embodiment, the products of the invention incorporate a first botanical compound that promotes the adherence of *Lactobacillus acidophilus* to the surface of skin or mucosa by at least about 50% in combination with a second botanical compound that promotes the adherence of *Staphylococcus epidermidis* to the surface of skin by at least about 50%.

In addition to promoting the adherence of *Lactobacillus acidophilus* and *Staphylococcus epidermidis*, it may also be beneficial to inhibit the adherence of at least one problem organism, such as *C. albicans, P. mirabilis*, and/or *P. aeruginosa*. Thus, the product may further incorporate a third botanical compound that inhibits the adherence of at least one organism to the surface of skin or mucosa, the organism selected from the group consisting of *Candida albicans, Proteus mirabilis*, and *Pseudomonas aeruginosa*, wherein the third botanical compound is capable of inhibiting the adherence of the organism to the surface of skin or mucosa by at least about 50%.

Such a combination may be further enhanced by incorproating into a product a fourth botanical compound that inhibits the growth of at least one problem organism, such as *Candida albicans, Proteus mirabilis*, and/or *Pseudomonas aeruginosa*. Thus, in one embodiment, the fourth botanical compound inhibits the growth of *Candida albicans* on or around the skin surface, the fourth botanical compound having an IC50 value of about 5% or less for *Candida albicans*. In another specific embodiment, the fourth botanical compound inhibits the growth of *Proteus mirabilis* on or around the skin surface, the fourth botanical compound having an IC50 value of about 5% or less for *Proteus mirabilis*. In yet another specific embodiment, the fourth botanical compound inhibits the growth of *Pseudomonas aeruginosa* on or around the skin surface, the fourth botanical compound having an IC50 value of about 5% or less for *Pseudomonas aeruginosa*.

Another beneficial combination would be to inhibit the adherence of at least one problem organism, such as *Candida albicans, Proteus mirabilis, Pseudomonas aeruginosa*, and/or *Staphylococcus epidermidis*, while at the same time inhibiting the growth of at least one problem organism, such as *Candida albicans, Proteus mirabilis, Pseudomonas aeruginosa*, and/or *Staphylococcus epidermidis*. Thus, in one embodiment, the products of the invention incorporate a first botanical compound that inhibits the adherence of at least one organism selected from the group consisting of *Candida albicans, Proteus mirabilis, Pseudomonas aeruginosa*, and/or *Staphylococcus epidermidis*, to the surface of skin or mucosa in combination with a second botanical compound that inhibits the growth of at least one organism selected from the group consisting of *Candida albicans, Proteus mirabilis, Pseudomonas aeruginosa*, and *Staphylococcus epidermidis*, on or around the skin surface. The first botanical compound is capable of inhibiting the adherence of the organism to the surface of skin or mucosa by at least about 50%, and the second botanical compound has an IC50 value of about 5% or less for *Candida albicans, Proteus mirabilis, Pseudomonas aeruginosa*, and/or *Staphylococcus epidermidis*.

The present invention is also directed to a wipe for use in wound care. The wipe comprises (a) a fibrous wipe substrate; (b) a first botanical compound that inhibits the adherence of *Staphylococcus epidermidis* to the surface of skin by at least about 50%; and (c) a second botanical compound that inhibits the growth of *Staphylococcus epidermidis* on or around the skin surface, the second botanical compound having an IC50 value of about 5% or less for *Staphylococcus epidermidis*.

In another specific embodiment, the present invention is directed to a wet wipe for promoting the adherence of *Lactobacillus acidophilus* to the surface of skin or mucosa. The wipe comprises a fibrous wipe substrate, a liquid formulation, and a botanical compound capable of increasing the adherence of *Lactobacillus acidophilus* to the surface of skin or mucosa by at least about 50%, wherein the liquid formulation is selected from the group consisting of a solution, a suspension, and an emulsion.

In addition to wipes and absorbent articles, the present invention is also directed to a method for selectively controlling the balance of flora on the skin. The method includes contacting a fibrous wipe substrate or absorbent substrate with the skin surface. The substrate includes a botanical compound for selectively controlling the growth and/or adherence of flora to the skin, wherein the compound promotes the adherence of at least one healthy flora to the surface of skin or mucosa, inhibits the growth of at least one problem flora on or around the skin surface, or inhibits the adherence of at least one problem flora to the surface of skin or mucosa, or any combination thereof. Additionally, a suitable method includes contacting a fibrous wipe substrate or absorbent substrate with the skin surface, wherein the substrate includes two or more botanical compounds for selectively controlling the growth and/or attachment of flora to the skin, wherein each compound promotes the adherence of at least one healthy flora to the surface of skin or mucosa, inhibits the growth of at least one problem flora on or around skin surface, or inhibits the adherence of at least one problem flora to the surface of skin or mucosa, or any combination thereof.

A more specific method involves promoting the adherence of *Lactobacillus acidophilus* to the surface of skin or mucosa. This method includes contacting a fibrous wipe substrate or absorbent substrate with the surface of skin or mucosa, wherein the substrate includes a botanical compound that is capable of increasing the adherence of *Lactobacillus acidophilus* to the surface of skin or mucosa by at least about 50%.

When present on a dry substrate, the botanical compound that selectively controls the balance of flora on skin is present in an amount of from about 0.01% (by weight of the treated substrate or product) to about 50% (by weight of the treated substrate or product), preferably from about 0.01% (by weight of the treated substrate or product) to about 10% (by weight of the treated substrate or product). When present as part of the liquid formulation used in combination with a wet wipe or absorbent article, the botanical compound is present in an amount of from about 0.01% (by total weight of the liquid formulation) to about 50% (by total weight of the liquid formulation), more preferably from about 0.01% (by total weight of the liquid formulation) to about 10% (by total weight of the liquid formulation).

Liquid formulations comprising botanical compounds, described herein, suitable for use in combination with a wipe or absorbent substrate can be solutions, suspensions, or emulsions. Many of the botanical compounds are substantially water-soluble or can be easily solubilized in water using techniques known to one skilled in the art to provide solutions comprising the botanical compound. Some botanical compounds described herein which are not substantially water-soluble or easily solubilized can be suspended or emulsified utilizing techniques known to one skilled in the art. Suitable emulsions include oil-in-water emulsions which can be prepared using suitable emulsifiers having an HLB greater than about 7 or can be water-in-oil emulsions prepared using suitable emulsifiers having an HLB of less than about 7. In order to sufficiently protect the water-soluble and/or hydrophilic compounds from premature oxidation during processing and/or product shelf storage, water-in-oil emulsions are typically particularly useful. The emulsified layer around the water phase can prevent oxygen from entering the water phase.

Alternatively or additionally, the botanical compounds can be encapsulated to prevent premature oxidation during process and product storage. Many encapsulation techniques known in the art can be utilized including those which provide sustained release, triggered release, targeted release or a combination of these release mechanisms. Other release mechanisms known in the art and suitable for use in accordance with the present invention include friction/pressure release, pH related release, water release, water evaporation release, and the like. Encapsulated botanical compounds can be delivered from both wet and dry wipe products. Suitable microencapsulation materials suitable for use in combination with the botanical compounds described herein include those available from Salvona, LLC (Dayton, N.J.).

Additionally, liposomes and/or nanosomes can be utilized to deliver and protect the botanical compounds described herein from premature oxidation in both a wet and a dry wipe product. As used herein, the terms liposomes and nanosomes are meant to include closed vesicles with walls composed of lipid-bilayer membranes to protect and deliver the core compound material.

Another method for delivering botanical compounds from a wet or dry wipe product or absorbent article and protecting these components from premature oxidation includes utilizing polymeric entrapment systems such as microspheres, microsponges, and polytraps such as those available from Advance Polymer Systems (Redwood City, Calif.). The botanical compound can be entrapped or adsorbed into the interstitial spaces of a polymer matrix thereby protecting the botanical compound from degredation and/or premature oxidation.

Particularly useful for delivering the botanical compound from dry substrates are semi-solid or solid formulations which transfer to the skin during use by the consumer. These formulations can be hydrophobic or hydrophilic in nature. The hydrophobic formulations are semi-solid or solid in nature at room temperature with a melting point greater than about 35° C. and contain from about 5 to about 95 weight percent of an emollient, from about 5 to about 95 weight percent of a solidifying agent such as an alpha olefin polymer, polyethylene, oxidized polyethylene, fatty alcohol, wax, or solid esters with a melting point of 35° C. or greater, from about 1 to about 50 weight percent of a viscosity enhancer such as silica, ethylene vinyl acetate copolymers, or an organo-clay and from about 0.1 to about 15 weight percent of an antioxidant agent.

The hydrophilic formulations are semi-solid or solid at room temperature with a melting point greater than about 35° C. and contain from about 30 to about 90 weight percent of a hydrophilic solvent/emollient such as water, propylene glycol, butylene glycol, low molecular weight (less than about 720) polyethylene glycols, dipropylene glycol glycerin, silicone glycols, methyl propanediol, or pentylene glycol, from about 10 to about 50 weight percent high molecular weight (greater than about 750) polyethylene glycol, from about 5 to about 40 weight percent of a fatty alcohol having from about 14 to about 30 carbons in the chain, optionally from about 1 to about 15 weight percent of a viscosity enhancer such as clays, glyceryl polyacrylates, or glyceryl polymethacrylates and from about 0.1 to about 15 weight percent of an antioxidant agent.

The dry wipe formulations can also be readily emulsifiable solid formulations with a melting point greater than about 35° C. and contain from about 5 to about 95 weight percent of a hydrophobic or hydrophilic emollient as set forth above, from about 5 to about 95 weight percent of a suitable solidifying agent as set forth above, from about 5 to about 25 weight percent of a suitable emulsifier and from about 1 to about 15 weight percent of an antioxidant agent. The suitable emulsifier can be anionic, cationic, amphoteric, zwitterionic, or nonioinic and combinations thereof.

In order to enhance consumer appeal, additional ingredients can be added to the above-described formulations. Suitable additional ingredients include, for example, anti-acne actives, antifoaming agents, antimicrobial actives, antifungal actives, antiseptic actives, antioxidants which prevent oxidation during processing and storage by preferentially oxidizing, astringents, colorants, deodorants, film formers, fragrances, moisturizers, skin protectants, sunscreen actives, and solvents.

The present invention is illustrated by the following examples which are merely for the purpose of illustration and are not to be regarded as limiting the scope of the invention or manner in which it may be practiced.

EXAMPLES

Various botanical compounds were tested to determine whether the botanical compound inhibited or enhanced bacterial or yeast attachment to the skin. Tests were also performed to determine if any of these botanical compounds exhibited antimicrobial activity. The botanical compounds and the combined results of these tests are set forth in Tables 1 and 2. Descriptions of the protocols for performing these tests are set forth in the following examples.

Example 1

Bacteria Kill Assay

The ability of various botanical compounds to inhibit the growth of *P. mirabilis, P. aeruginosa*, and *S. epidermidis*, was tested. This protocol can also be applied to test the ability of botanical compounds to inhibit the growth of other bacteria, in addition to those tested herein.

To begin, a 10% solution of each botanical in trypticase soy broth (TSB) was prepared by adding either 1 ml or 1 g of botanical to 9 or 10 ml TSB, respectively. Two-fold dilutions of the botanical solutions were performed in a 96 well plate. The dilutions were performed as follows:

10%: 100 ul of the 10% stock is added to the well
5%: 50 ul from the 10% well plus 50 ul TSB
2.5%: 50 ul from the 5% well plus 50 ul TSB
1.25%: 50 ul from the 2.5% well plus 50 ul TSB
0.625%: 50 ul from the 1.25% well plus 50 ul TSB
0.3125%: 50 ul from the 0.625% well plus 50 ul TSB The final volume in each well was 50 ul after discarding 50 ul from the 0.3125% dilution. All experiments were done in triplicate.

*P. mirabilis* (ATCC #29906), *P. aeruginosa* (ATCC #27853), or *S. epidermidis* (ATCC #12228) were cultured overnight. The overnight culture was diluted with TSB to a concentration of about $1\times10^6$ cells/ml. 50 µl of this diluted bacterial culture was added to each well containing the diluted botanical solutions, to form sample solutions comprising diluted bacterial cultures at the concentrations described above and the diluted botanical solution. 50 µl of this diluted bacterial culture was also added to 50 µl TSB and used as a negative control. The optical density (650 nm) of the control and the samples was determined using a spectrophotometer. Both the control and the sample were then incubated for 16 to 18 hours at 37° C., with agitation at about 400 rpm. The wells were again inserted into the spectrophotometer, and further shaken. The optical density (650 nm) of the control and the sample was read again. The percentage of bacterial growth in the sample relative to the control was determined by the following equation:

$[(OD_{650}$ sample @18 hours$-OD_{650}$ sample @0 hours$)/(OD_{650}$ bacteria only @18 hours$-OD_{650}$ bacteria only @0 hours$)]*100$ The results for the three wells comprising each dilution step were averaged. The results were plotted, and an IC50 value for each botanical compound was determined.

The results are given in Table 2, which shows the effect of various botanical compounds on the growth of *C. albicans, P. aeruginosa, P. mirablis*, and *S. epidermidis* relative to a negative control (compounds not tested are marked with a dash). The lower the IC50 value, the more potent a growth inhibitor the botanical compound was. An IC50 value of greater than 10% indicates that no growth inhibition was observed. Botanical compounds with an IC50 value of 10% or less showed some ability to inhibit growth. However, for purposes of the present invention, botanical compounds that have an IC50 value of about 5% or less are considered growth inhibitors.

Example 2

Yeast Kill Assay

The ability of various botanical compounds to inhibit the growth of *C. albicans* was tested. The protocol described herein can also be applied to test the ability of botanical compounds to inhibit the growth of other yeast, in addition to *C. albicans*.

To begin, a 10% solution of each botanical in TSB was prepared by adding either 1 ml or 1 g of botanical to 9 or 10 ml TSB, respectively. Dilutions were performed, as described in Example 1.

*C. albicans* (ATCC #10231) was cultured overnight. The overnight culture was diluted with TSB to a concentration of about $1\times10^6$ cells/ml. 50 µl of this diluted yeast culture was added to each well containing the diluted botanical solutions, to form sample solutions comprising diluted yeast cultures at the concentrations described above and the diluted botanical solution. 50 µl of this diluted yeast culture was also added to 50 µl TSB and used as a negative control. The optical density (650 nm) of the control and the samples was determined using a spectrophotometer. Both the control and the sample were then incubated for 16 to 18 hours at 37° C., with agitation at about 400 rpm. The wells were again inserted into the spectrophotometer, and further shaken. The optical density (650 nm) of the control and the sample was read again. The percentage of yeast growth in the sample relative to the control was determined by the following equation:

$[(OD_{650}$ sample @18 hours$-OD_{650}$ sample @0 hours$)/(OD_{650}$ yeast only @18 hours$-OD_{650}$ yeast only @0 hours$)]*100$ The results for the three wells comprising each dilution step were averaged. The results were plotted, and an IC50 value for each botanical compound was determined. The results are given in Table 2, as described in Example 1.

Example 3

Adhesion Assay for *P. Mirabilis, S. Epidermidis*, and *P. Aeruginosa*

Each of the botanical compounds listed in Table 1 was screened to measure the effect of the compound on the adhesion of *P. mirabilis, S. epidermidis*, or *P. aeruginosa* to the skin. The protocol described herein can also be applied to test the effect of botanical compounds on the adhesion of other bacteria to the skin.

Two days prior to the screen, a bacterial culture of either *P. mirabilis* (ATCC #29906), *S. epidermidis* (ATCC #12228), or *P. aeruginosa* (ATCC #27853) was prepared. One frozen bead of bacteria was added to 10 ml of TSB, and grown overnight at 37° C. with agitation at 100 rpm. A synthetic skin substrate (VITRO-SKIN® substrate) was placed in a hydration chamber overnight.

One day prior to the screen, discs of the synthetic skin, sized to fit the wells of a 96 well plate, were cut out in a controlled humidity room using a #2 tool. The discs were placed in the wells of the plate, and the plate was stored in a humidity chamber. A TSB culture was prepared by inoculating TSB with the overnight culture, previously described, at a ratio of 1:1000 (overnight culture:TSB). The TSB culture was then grown overnight at 37° C. with agitation at 100 rpm. A 10% solution of each botanical in TSB was prepared by adding either 100 µl of botanical to 900 µl TSB, or if the botanical was a solid, using 100 mg of botanical and a sufficient amount of TSB to bring the total volume to 1 ml. 10% Tween® 20 stock in TSB was prepared as a positive control by adding 100 µl of Tween® 20 to the appropriate amount of TSB, to give a 10% solution.

The next day, the optical density (650 nm) of the TSB culture was read. It was assumed that 1 OD was equal to $1\times10^8$ cells/ml. The culture was centrifuged at 5,000×g for 10 minutes to pellet the bacteria. The bacteria were resuspended in a sufficient amount of TSB, so that the final concentration of bacteria was $1\times10^6$ cells/ml. 50 µl of either the 10% botanical stock or the control solution was added to wells containing the synthetic skin substrate. 50 µl of the bacteria in TSB was then added to each of these wells, and the cells were allowed to adhere to the synthetic skin for three hours at room temperature, shaking slowly. After three hours, the solutions were removed from the wells, and the synthetic skin was washed three times with a solution of 250 µl of phosphate buffered saline (PBS) plus 0.05% Tween® 20. The skin was transferred to a white plate, and 200 µl of 10% AlamarBlue® dye in TSB was added to each well. The plate was incubated at 37° C. AlamarBlue® levels were read (emission levels read at 590 nm) in an Ascent plate reader (excitation level of 544 nm) at 1 and 2 hours. When not being read, the plate was incubated at 37° C. with a lid.

Results are given in Table 1, which gives the percent adherence to the skin of *P. mirabilis, S. epidermidis, P. aeruginosa, L. acidophilus*, and *C. albicans* for the various botanical compound samples, relative to the control. The percentage is based on the number of cells that adhered to the skin for the botanical samples as compared to the number of cells that adhered to the skin in the control, as determined by the AlamarBlue® levels. A percentage greater than 100% indicated that more cells adhered with the botanical sample than with the control; a percentage less than 100% indicated that fewer cells adhered with the botanical sample than with the control. For purposes of the present invention, if the percentage is 150% or greater, the botanical compound is considered to be an adherence promoter for the particular organism; if the percentage is 50% or lower, the botanical compound is considered to be an anti-adherent for the particular organism.

Some of the compounds in Table 2 that are listed as growth inhibitors for certain organisms have a percent adherence of less than 50% for that organism. In this situation, no conclusion can be drawn as to the anti-adherent properties of the botanical compound, as it is unclear whether the low percent adherence is due to anti-adherent properties of the botanical compound, or to the compound's growth inhibiting properties.

Example 4

Adhesion Assay for *Lactobacillus Acidophilus*

Each of the compounds listed in Table 1 was screened to measure the effect of the compound on the adhesion of *Lactobacillus acidophilus* to the skin.

Two days prior to the screen, a bacterial culture of *Lactobacillus acidophilus* was prepared. One frozen bead of *Lactobacillus acidophilus* (ATCC #:314) was added to 10 mL of *Lactobacilli* broth, and the culture was incubated overnight at 37° C. A synthetic skin substrate (VITRO-SKIN® substrate) was placed in a hydration chamber overnight.

One day prior to the screen, discs of the synthetic skin, sized to fit the wells of a 96 well plate, were cut out using a #2 tool. The discs were placed in the wells of the plate, and the plate was stored in a humidity chamber. A *Lactobacilli* broth culture was prepared by inoculating *Lactobacilli* broth with the overnight culture, previously described, at a ratio of 1:1000 (overnight culture: *Lactobacilli* broth). The *Lactobacilli* broth culture was grown overnight at 37° C. A 10% solution of each botanical in TSB was prepared by adding either 1 ml of botanical to 9 ml TSB, or if the botanical was a solid, using 1 g of botanical and a sufficient amount of TSB to bring the total volume to 10 ml. 10% Tween® 20 stock in TSB was prepared as a positive control, by adding 1 mL Tween® 20 to 9 ml of TSB.

The next day, the optical density (650 nm) of the *Lactobacilli* broth culture was read. 1 OD is approximately $1\times1^9$ cells/ml. The culture was centrifuged at 5,000×g for 10 minutes to pellet the bacteria. The bacteria were resuspended in a sufficient amount of TSB, so that the final concentration of bacteria was $1\times10^6$ cells/ml. 50 µl of either the 10% botanical stock or the control solution was added to wells containing the synthetic skin substrate. 50 µl of the bacteria in *Lactobacilli* broth was then added to each of these wells, and the cells were allowed to adhere to the synthetic skin for three hours at either 33° C. or 37° C. After three hours, the solutions were removed from the wells, and the synthetic skin was washed in the wells three times with a solution of 250 µl of PBS plus 0.05% Tween® 20. The skin was transferred to a white plate, and 200 µl of 10% AlamarBlue® dye in TSB was added to each well. The plate was incubated at 37° C. AlamarBlue® levels were read (emission levels read at 590 nm) in an Ascent plate reader (excitation level of 544 nm) at 2 and 3 hours. When not being read, the plate was incubated at 37° C. with a lid.

Results are given in Table 1, which is described in Example 3.

Example 5

Adhesion Assay for *Candida Albicans*

Each of the compounds listed in Table 1 was screened to measure the effect of the compound on the adhesion of *C. albicans* to the skin. The protocol described herein can also be applied to test the effect of botanical compounds on the adhesion of other yeast to the skin.

Two days prior to the screen, a culture of *C. albicans* was prepared. One frozen bead of *C. albicans* (ATCC #10231) was added to 10 ml Saboraud's dextrose broth ("SDB"), and grown overnight at 37° C. with agitation at 150 rpm. A synthetic skin substrate (VITRO-SKIN® substrate) was placed in a hydration chamber overnight.

One day prior to the screen, discs of the synthetic skin, sized to fit the wells of a 96 well plate, were cut out in a controlled humidity room using a #2 tool. The discs were placed in the wells of the plate, and the plate was stored in a humidity chamber. A SDB culture was prepared by inoculating SDB with the overnight culture, previously described, at a ratio of 1:1000 (overnight culture:SDB). The SDB culture was then grown overnight at 37° C. with agitation at 150 rpm. A 10% solution of each botanical in TSB was prepared by adding either 1 ml of botanical to 9 ml TSB, or if the botanical was a solid, using 1 g of botanical and a sufficient amount of TSB to bring the total volume to 10 ml. 10% Tween® 20 stock in TSB was prepared as a positive control, by adding 1 mL of Tween® 20 to 9 ml of TSB.

The next day, the optical density (650 nm) of the SDB culture was read. It was assumed that 1 OD equals $1\times10^8$ cells/ml. The culture was centrifuged at 5,000×g for 10 minutes to pellet the yeast. The yeast were resuspended in a sufficient amount of TSB, so that the final concentration of yeast was $1\times10^6$ cells/ml. 50 µl of either the 10% botanical stock or the control solution was added to the wells containing the synthetic skin substrate. 50 µl of the yeast in TSB was then added to each of these wells, and the cells were allowed to adhere to the synthetic skin for three hours at 33° C., shaking slowly. After three hours, the solutions were removed from the wells, and the syntehtic skin was washed in the wells three times with a solution of 250 µl of PBS plus 0.05% Tween 20.

The skin was transferred to a white plate, and 200 μl of 10% AlamarBlue® dye in TSB was added to each well. The plate was incubated at 37° C. AlamarBlue® levels were read (emission levels read at 590 nm) in an Ascent plate reader (excitation level of 544 nm) at 2 and 3 hours. When not being read, the plate was incubated at 37° C. with a lid.

Results are given in Table 1, which is described in Example 3.

TABLE 1

Effect of Botanical Compounds on Attachment of *C. albicans* (CA), *P. aeruginosa* (PA), *P. mirabilis* (PM), *S. epidermidis* (SE), and *L. acidophilus* (LA) to Skin

| Botanical Compound | PM | PA | SE | CA | LA |
|---|---|---|---|---|---|
| Aloe Ferox HS | 18.3 | 119.5 | 14.9 | 13.7 | 244.2 |
| Aloe Gel | 100.7 | 150.5 | 82.6 | 98.2 | 581.7 |
| American Ginseng | 124.3 | 83.9 | 80.6 | 42.2 | 370.3 |
| Angelica Root PE 4:1 | 225.3 | 119.1 | 257.1 | 7.4 | 141.9 |
| Arkin Special | 131.6 | 92.9 | 25.3 | 29.1 | 146.4 |
| Arnica MCF 1157 Hydro | 267.5 | 109.0 | 129.9 | 65.1 | 55.1 |
| Biodynes TRF Improved | 172.2 | 56.1 | 192.0 | 80.0 | 116.2 |
| Bleuet MCF 783 Hydro | 69.1 | 125.0 | 242.9 | 76.7 | 56.1 |
| Butcher's Broom | 74.3 | 124.1 | 114.7 | 156.1 | 133.0 |
| Calendula (Marigold) | 66.5 | 86.9 | 55.8 | 69.1 | 1106.8 |
| Calendula MCF 774 | 152.3 | 141.0 | 61.8 | 112.2 | 166.5 |
| Canadian Willowherb | 46.8 | 103.7 | 4.9 | 152.8 | 3176.7 |
| Cat's Claw | 24.1 | 153.5 | 15.3 | 55.6 | 1161.7 |
| Centella | 141.6 | 123.5 | 90.2 | 190.0 | 857.0 |
| Chamomile | 162.8 | 75.2 | 46.1 | 84.8 | 398.5 |
| Chamomile CL | 52.4 | 127.1 | 48.2 | 151.3 | 147.1 |
| Chamomile Distillate | 86.7 | 174.6 | 81.0 | 78.0 | 132.8 |
| Chlorella | 168.6 | 132.6 | 51.3 | 95.9 | 69.4 |
| Ceramide Complex | 52.8 | 37.6 | 58.3 | 145.7 | 1772.7 |
| Comfey Leaves | 98.8 | 88.4 | 46.5 | 14.3 | 168.1 |
| Cromoist 0–25 | 108.0 | 147.9 | 60.0 | 101.2 | 317.6 |
| Cromoist HYA | 41.8 | 105.7 | 11.6 | 77.0 | 291.0 |
| Dandelion | 75.0 | 93.0 | 61.2 | 74.7 | 187.3 |
| Devil's Claw | 82.8 | 141.4 | 32.1 | 79.5 | 755.9 |
| Dong Quai | 81.6 | 121.4 | 90.0 | 32.4 | 750.8 |
| Drago-Oat Active | 90.8 | 87.7 | 70.6 | 55.7 | 468.4 |
| Echinacea Dry Aq. | 4.8 | 0.6 | 41.4 | 21.8 | 1575.5 |
| Gingko Biloba | 19.4 | 92.4 | 22.2 | 108.2 | 614.6 |
| Ginseng GR 471 Hydro | 107.1 | 144.0 | 57.6 | 130.3 | 385.9 |
| Glucosamine 99 | 79.0 | 61.0 | 62.3 | 13.9 | 170.3 |
| Goldenseal | 88.8 | 99.2 | 16.9 | 5.5 | 954.0 |
| Gotu Kola PG 5:1 | 94.1 | 135.1 | 26.1 | 63.8 | 268.6 |
| Grape Seed | 86.3 | 91.6 | 58.6 | 8.3 | 2072.4 |
| Grape Seed Extract | 2.2 | −0.9 | 22.7 | 28.3 | −14.8 |
| Green Tea | 0.5 | 37.7 | 8.0 | 4.9 | 405.3 |
| Green Tea Conc. | 113.3 | 87.6 | 141.7 | 22.3 | −312.9 |
| Green Tea Extr. | −0.6 | 2.0 | 77.5 | 10.9 | 116.86 |
| Green Tea HS | 28.5 | 82.3 | 53.1 | 20.8 | 136.24 |
| Hexaplant Richter | 73.6 | 73.9 | 142.6 | 67.8 | 111.64 |
| Hydrocotyle GR 040 | 83.4 | 65.3 | 155.3 | 105.9 | 86.82 |
| Hydrolactin 2500 | 10.1 | 91.2 | 180.0 | 120.4 | 60.89 |
| Hydrolite-5 | 9.2 | 5.1 | 141.5 | 3.9 | 169.66 |
| Hydrosoy 2000 SF | 44.2 | 73.2 | 38.8 | 68.1 | 383.10 |
| Lamier Blanc MCF 796 | 97.3 | 78.2 | 147.0 | 116.7 | 95.76 |
| Lavendar MCF 1484 | 97.9 | 81.7 | 224.7 | 48.8 | 45.91 |
| Lime Blossom | 60.5 | 64.0 | 198.3 | 50.4 | 12.62 |
| Lime Blossom Distillate | 90.0 | 101.5 | 241.0 | 73.2 | 27.30 |
| Marigold (Calendula) | 53.1 | 89.6 | 199.5 | 52.9 | 67.22 |
| Marron D'Inde MCF 1972 | 27.5 | 104.3 | 37.3 | 33.3 | 59.91 |
| Marron D'Inde (Horse Chestnut) | 5.9 | 113.7 | 21.0 | 48.9 | 193.37 |
| Matricaire (German Chamomile) | 113.9 | 101.6 | 158.5 | 215.2 | 83.4 |
| Melilot GR 436 | 91.7 | 93.2 | 123.6 | 205.9 | 168.0 |
| Milk Thistle | 100.7 | 65.2 | 52.7 | 145.6 | 163.0 |
| Nab Willowbark Extr. | 60.7 | 6.3 | 80.9 | 117.7 | 685.1 |
| NSLE Lipomicron | 18.8 | 17.9 | 109.6 | 94.8 | 110.2 |
| Phytexcell Arnica | 141.0 | 102.5 | 207.0 | 286.6 | 95.1 |
| Phytexcell Mulberry | 87.2 | 88.6 | 88.7 | 135.3 | 57.3 |
| Pineapple B | 7.6 | 1.3 | 2.7 | 16.4 | −3.7 |
| Purple Coneflower | 136.7 | 60.5 | 96.4 | 173.5 | 35.7 |
| Sage CL | 53.9 | 57.9 | 84.2 | 68.2 | 82.0 |

TABLE 1-continued

Effect of Botanical Compounds on Attachment of *C. albicans* (CA), *P. aeruginosa* (PA), *P. mirabilis* (PM), *S. epidermidis* (SE), and *L. acidophilus* (LA) to Skin

| Botanical Compound | PM | PA | SE | CA | LA |
|---|---|---|---|---|---|
| Sage GW | 73.0 | 64.7 | 108.7 | 86.9 | 83.5 |
| Sage Special | 118.3 | 73.1 | 153.0 | 58.3 | 112.1 |
| Sandal Complex | 14.8 | 5.9 | 56.3 | 18.4 | 140.8 |
| Sapoinaire LC 386 | 102.5 | 118.0 | 138.2 | 181.0 | 91.3 |
| Sea Parsley | 87.9 | 150.0 | 69.3 | 86.8 | 1506.8 |
| Sedaplant Richter | 120.0 | 138.0 | 152.8 | 260.5 | 1304.3 |
| Soluble Wheat Protein | 80.9 | 21.7 | 28.6 | 38.8 | 216.9 |
| Spirulina | 142.6 | 123.7 | 58.9 | 127.5 | 1769.5 |
| St. John's Wort W/S | 65.1 | 138.9 | 19.3 | 77.5 | 704.3 |
| White Mistle Toe | 96.7 | 116.6 | 49.5 | 100.8 | 896.8 |
| Witchhazel CL | 50.2 | 145.5 | 59.5 | 246.0 | 4045.1 |
| Witchhazel Distillate | 117.4 | 120.4 | 109.3 | 117.2 | 624.8 |
| Witchhazel GW | −24.1 | 116.2 | 124.5 | 65.5 | 1220.1 |
| Yarrow | 160.6 | 145.8 | 34.2 | 91.5 | 750.8 |
| Yucca 70 | 13.6 | 0.4 | 26.5 | 0.6 | 3574.7 |
| Yucca Extr. Powder 50% | 16.1 | 27.0 | 58.3 | 14.3 | 906.1 |

TABLE 2

Effect of Selected Botanical Compounds on the Growth of *C. albicans* (CA), *P. aeruginosa* (PA), *P. mirabilis* (PM), and *S. epidermidis* (SE) (IC50 values)

| Botanical Compound | CA | PA | PM | SE |
|---|---|---|---|---|
| *Aloe* Ferox HS | >10% | — | 8.30% | 5.00% |
| American Ginseng | >10% | — | — | — |
| Angelica Root PE 4:1 | 7.90% | — | — | — |
| Arkin Special | >10% | — | — | >10% |
| Canadian Willowherb | — | — | 4.70% | 4.70% |
| Cat's Claw | — | — | >10% | >10% |
| Chamomile | — | — | — | >10% |
| Chamomile CL | — | — | — | 4.90% |
| Ceramide Complex | — | >10% | — | — |
| Comfey Leaves | 6.10% | — | — | >10% |
| Cromoist HYA | — | — | >10% | 7.30% |
| Devil's Claw | — | — | — | >10% |
| Dong Quai | >10% | — | — | — |
| Echinacea Dry Aq. | 2.50% | 5.80% | 5.80% | 5.30% |
| Gingko Biloba | — | — | 3.30% | >10% |
| Glucosamine 99 | 1.90% | — | — | — |
| Goldenseal | 1.8% | — | — | 1.80% |
| Gotu Kola PG 5:1 | — | — | — | >10% |
| Grape Seed | >10% | — | — | — |
| Grape Seed Extract | 0.20% | 0.30% | 0.20% | 0.40% |
| Green Tea | 3.50% | >10% | >10% | 3.80% |
| Green Tea Conc. | 0.30% | — | — | — |
| Green Tea Extr. | 0.10% | 1.80% | >10% | — |
| Green Tea HS | >10% | — | >10% | — |
| Hydrolactin 2500 | — | — | >10% | — |
| Hydrolite-5 | 8.30% | 2.20% | 2.00% | — |
| Hydrosoy 2000 SF | — | — | >10% | >10% |
| Lavendar MCF 1484 | >10% | — | — | — |
| Marron D'Inde MCF 1972 | >10% | — | >10% | >10% |
| Marron D'Inde (Horse Chestnut) | >10% | — | >10% | >10% |
| Nab Willowbark Extr. | — | 9.60% | — | — |
| NSLE Lipomicron | — | 6.00% | 5.40% | — |
| Pineapple B | >10% | 8.10% | >10% | 1.30% |
| Sandal Complex | >10% | 9.70% | >10% | — |
| Soluble Wheat Protein | >10% | 9.80% | — | >10% |
| St. John's Wort W/S | — | — | — | >10% |
| White Mistle Toe | — | — | — | >10% |
| Witchhazel GW | — | — | >10% | — |
| Yarrow | — | — | — | >10% |
| *Yucca* 70 | 8.20% | >10% | 1.80% | 6.40% |
| *Yucca* Extr. Powder 50% | 7.70% | >10% | >10% | — |

TABLE 3

| Name | Company | Address | Lot | Catalog |
|---|---|---|---|---|
| *Aloe* Ferox HS | Alban Muller International | Northvale, NJ | 7114158 | 64453 |
| *Aloe* Gel | Tri-K Industries | Northvale, NJ | 970217 | |
| Amercian Ginseng | Bio-botanica | Hauppauge, NY | 951340 | 9865 |
| Angelica Root PE 4:1 | Bio-botanica | Hauppauge, NY | 921653 | 401250 |
| Apple GT | Dragoco | Totowa, NJ | 2/037050 | L742477 |
| Arkin Special | Dragoco | Totowa, NJ | 2/032581 | L647147 |
| Arnica MCF 1157 Hydro | Gattefosse | Cedex, France | 23043 | 5005 |
| Arnica Special | Dragoco | Totowa, NJ | 2/034591 | L641060 |
| Avocado | Dragoco | Totowa, NJ | 2/034599 | L645246 |
| AVocado GW | Dragoco | Totowa, Nj | 2/031170 | L603922 |
| Biodynes TRF Improved | Brooks Industries | South Plainfield, NJ | 3965 | |
| Black Currant B | Dragoco | Totowa, NJ | 2/036100 | P331166 |
| Black Currant GT | Dragoco | Totowa, NJ | 2/037100 | P331166 |
| Bleuet MCF 783 Hydro (cornflower) | Gattefosse, | Cedex, France | 23593 | 5009 |
| Butcher's Broom HS | Alban Muller International | Northvale, NJ | 8025951 | 66363 |
| *Calendula* (Marigold) | Bell Flavors & Fragrances, Inc. | Northbrook, IL | Req: 062169 | |
| *Calendula* MCF 774 Hydro | Gattefose | Cedex, France | 24243 | 5015 |
| Canadian Willowherb | Fytokem | Saskatoon, Canada | 971015-P | |
| Cat's Claw | Bio-botanica | Hauppauge, NY | 951341 | 9945A |
| Centella | Bio-botanica | Hauppauge, NY | 981177 | 9869A |
| Ceramide Complex Cir | Chemisches Laboratorium | Berlin | 732207 | |
| Chamomile | Bio-botanica | Hauppauge, NY | 980572 | 9831 |
| Chamomile CL | Dragoco | Totowa, NJ | 2/033026 | L659226 |
| Chamomile Distillate | Dragoco | Totowa, NJ | 2/380930 | L659743 |
| Chamomile Special | Dragoco | Totowa, NJ | 2/033021 | 694633 |
| Chlorella | Bio-botanica | Hauppauge, NY | 951289 | 9835 |
| Comfrey Leaves | Bell Flavors & Fragrances, Inc. | Northbrook, IL | Req: 062565 | |
| Cranberry B | Dragoco | Totowa, NJ | 2/036600 | P15193 |
| Cranberry GT | Dragoco | Totowa, NJ | 2/037600 | 4100723 |
| Crolastin | Croda | Parsippany, NJ | 0526 | |
| Cromoist 0–25 (Hydrolyzed whole oats) | Croda | Parsippany, NJ | 8172 | |
| Cromoist Hya | Croda | Parsippany, NJ | 7922/1 | |
| Dandelion | Active organics | | S72041A | 816310-11 |
| Devil's Claw | Indena-International Sourcing | Uppersaddle River, NJ | EG522 | |
| Dong Quai | Active organics Glenn Corp. | Lewisville, TX | S64418B | 316320-11 |
| Drago-Oat-Active | Dragoco | Totowa, NJ | 2/060900 | 25493 |
| Echinacea Dry Aqueous Ext | MMP, Inc. | | 7329 | |
| Garcinia | Bio-botanica | Hauppauge, NY | 951283 | 9861 |
| Ginkgo Biloba | Bio-botanica | Hauppauge, NY | 951286 | 9861A |
| Ginseng GR 471 Hydro | Gattefosse | Cedex, France | 23268 | 5030 |
| Glucosamine 99 | Sher-Mar Enterprises | San Diego, CA | | |
| Goldenseal | Bio-botanica | Hauppauge, NY | 951338 | 9868 |
| Gotu Kola PG 5:1 | Bio-botanica | Hauppauge, NY | | |
| Grape Seed | Active organics Glenn Corp. | Lewisville, TX | S76920B | 318650-11 |
| Grape Seed Extract | Dragoco | Totowa, NJ | 2/03199 | P17400 |

TABLE 3-continued

Source of Botanical Compounds

| Name | Company | Address | Lot | Catalog |
|---|---|---|---|---|
| Grapefruit B | Dragoco | Totowa, NJ | 2/036150 | L4100313 |
| Grapefruit GT | Dragoco | Totowa, NJ | 2/037150 | L4100211 |
| Green Tea | Bio-botanica | Hauppauge, NY | | 9945 |
| Green Tea Conc. | Active organics Glenn Corp. | Lewisville, TX | 308463 | 300230-94 |
| Green Tea Extract | Dragoco | Totowa, NJ | 2/031598 | 3066 |
| Green Tea HS | Alban Muller International | Northvale, NJ | 7114309 | |
| Hexaplant Richter | Chemisches Laboratorium | Berlin | 732431 | 243 |
| *Hibiscus* Special | Dragoco | Totowa, NJ | 2/033115 | L851028 |
| Hydrocotyle GR 040 Hydro (hydrocotyl) | Gattefosse | Cedex, France | 22842 | 5038 |
| Hydrolactin 2500 | Croda | Parsippany, NJ | 7034D | |
| Hydrolite-5 | Dragoco | Totowa, NJ | 2/016020 | 27033 |
| Hydrosoy 2000 S.F. | Croda | Parsippany, NJ | 1278 | |
| Lamier Blanc MCF 796 Hydro (White Nettle) | Gattefosse | Cedex, France | 22571 | 5040 |
| Lavener MCF 1484 Hydro | Gattefosse | Cedex, France | 25872 | |
| Lime Blossom CL | Dragoco | Totowa, NJ | 2/033093 | L644049 |
| Lime Blossom Distillate | Dragoco | Totowa, NJ | 2/382920 | L659568 |
| Lys MCF 1968 Hydro (lily) | Gattefosse | Cedex, France | 23410 | 5044 |
| Marigold (*Calendula*) | Bell Flavors & Fragrances, Inc. | Northbrook, IL | 62565 | B-2924 |
| Marron D'Inde MCF 1972 Hydro (Horse Chestnut) | Gattefosse | Cedex, France | 22043 | 5046 |
| Marronnier D'Inde (Horse Chestnut) | Indea-International Sourcing | Uppersaddle River, NJ | EG042 | |
| Matricaire (German Chamomille) | Indea-International Sourcing | Uppersaddle River, NJ | EG004 | |
| Melilot GR 436 Hydro (Sweet Clover) | Gattefosse | Cedex, France | 23316 | 5051 |
| Milk Thistle | Active organics Glen Corp. | Lewisville, TX | S76894A | 344000-11 |
| Nab Willow Bark Extract | Brooks Industries | South Plainfield, NJ | 28392 | |
| NSLE Lipomicron | Sederma | France | NSLE1032 | |
| Orange B | Dragoco | Totowa, NJ | 2/036400 | P327911 |
| Organe GT | Dragoco | Totowa, NJ | 2/037400 | P327911 |
| Papaya B | Dragoco | Totowa, NJ | 2/036450 | L8102475 |
| Phytexcell Arnica | Croda | Parsippany, NJ | 972 | 34656 |
| Phytexcell Mulberry | Croda | Parsippany, NJ | 1004 | 34684 |
| Phytoplenolin | Bio-botanica | Hauppauge, NY | 980510 | 9870 |
| Pineapple B | Dragoco | Totowa, NJ | 2/036000 | 728754 |
| Purple Coneflower | Bio-botanica | Hauppauge, NY | 951338 | 9852 |
| Sage CL | Dragoco | Totowa, NJ | 2/033294 | L640225 |
| Sage GW | Dragoco | Totowa, NJ | 2/031770 | L619604 |
| Sage Special | Dragoco | Totowa, NJ | 2/033291 | P312506 |
| Sandal Complex | Dragoco | Totowa, NJ | 2/B04081 | 132360 |
| Saponaire LC 386 Hydro (*Saponaria*) | Gattefosse | Cedex, France | 24418 | 5070 |

TABLE 3-continued

Source of Botanical Compounds

| Name | Company | Address | Lot | Catalog |
|---|---|---|---|---|
| Sea Parsley | Phillip rockley, Ltd. | | A81 | R10418 |
| Sedaplant Richter | Chemisches Laboratorium | Berlin | 732384 | 460 |
| Soluble Wheat Proten (tritisol) | Croda | Parsippany, NJ | 0017 | |
| Spirulina | Bio-botanica | Hauppauge, NY | 951288 | 9837 |
| St. John's Wort W/S | Dragoco | Totowa, NJ | 2/032985 | L658926 |
| White Mistle Toe | Dragoco | Totowa, NJ | 2/033141 | L653324 |
| Witchhazel CL | Dragoco | Totowa, NJ | 2/033900 | 723422 |
| Witchhazel Distillate | Dragoco | Totowa, NJ | 2/365470 | L638489 |
| Witchhazel GW | Dragoco | Totowa, NJ | 2/031340 | L651033 |
| Yarrow | Bio-botanica | Hauppauge, NY | 951336 | 9958 |
| Yucca 70 | Sher-Mar Enterprises | San Diego, CA | | |
| Yucca Extract Powder (50%) | Garuda | Santa Cruz, Ca | 557-98226-DE | YUCEXT50 |

What is claimed is:

1. A product for promoting the adherence of *Lactobacillus acidophilus* to the surface of skin or mucosa, the product comprising:
   a) a substrate selected from the group consisting of a fibrous wipe substrate and an absorbent substrate; and
   b) a first botanical compound capable of increasing the adherence of *Lactobacillus acidophilus* to the surface of skin or mucosa by at least about 50%, wherein the first botanical compound is Sea Parsley; and
   c) a second botanical compound capable of inhibiting the adherence of an organism to the surface of skin or mucosa by at least about 50%, wherein the organism is selected from the group consisting of *Candida albicans, Proteus mirabilis, Pseudomonas aeruginosa, Staphylococcus epidermidis*, and combinations thereof, the second botanical compound being selected from the group consisting of Dong Quai, Goldenseal, Grape Seed, Grape Seed Extract, and combinations thereof.

2. The product as set forth in claim 1 wherein the product is selected from the group consisting of a feminine wipe, a feminine napkin, a tampon, and an interlabial pad.

3. The product as set forth in claim 1 wherein the first botanical compound is present on the substrate in an amount of from about 0.01% (by weight of the treated substrate) to about 50% (by weight of the treated substrate).

4. The product as set forth in claim 3 wherein the first botanical compound is present on the substrate in an amount of from about 0.01% (by weight of the treated substrate) to about 10% (by weight of the treated substrate).

5. The product as set forth in claim 1 wherein the product is a wipe, the wipe further comprising a liquid formulation, wherein the first botanical compound is present in the liquid formulation in an amount of from about 0.01% (by total weight of the liquid formulation) to about 50% (by total weight of the liquid formulation).

6. The product as set forth in claim 1 further comprising a third botanical compound capable of inhibiting the growth of the organism on or around the skin surface, wherein the third botanical compound has an IC50 value of about 5% or less for the organism.

7. A product for inhibiting the growth of at least one organism on or around the skin surface, the product comprising:
   a) a substrate selected from the group consisting of a fibrous wipe substrate and an absorbent substrate;
   b) a first botanical compound that has an IC50 value of about 5% or less for the organism, the first botanical compound being selected from the group consisting of Canadian Willowherb, Gingko Biloba, Goldenseal, Grape Seed Extr., and combinations thereof;
   wherein the organism is selected from the group consisting of *Proteus mirabilis, Pseudomonas aeruginosa, Candida albicans*, and *Staphylococcus epidermidis*; and
   c) a second botanical compound capable of increasing the adherence of *Lactobacillus acidophilus* to the surface of skin or mucosa by at least about 50%, wherein the second botanical compound is Sea Parsley.

8. The product as set forth in claim 7 wherein the first botanical compound is present on the substrate in an amount of from about 0.01% (by weight of the treated substrate) to about 50% (by weight of the treated substrate).

9. The product as set forth in claim 8 wherein the first botanical compound is present on the substrate in an amount of from about 0.01% (by weight of the treated substrate) to about 10% (by weight of the treated substrate).

10. The product as set forth in claim 7 wherein the product is a wipe, the wipe further comprising a liquid formulation, wherein the first botanical compound is present in the liquid formulation in an amount of from about 0.01% (by total weight of the liquid formulation) to about 50% (by total weight of the liquid formulation).

11. The product as set forth in claim 6 wherein the first botanical compound, second botanical compound, and third botanical compound are encapsulated.

12. A product for inhibiting the adherence of at least one organism to the surface of skin or mucosa, the product comprising:
   a) a substrate selected from the group consisting of a fibrous wipe substrate and an absorbent substrate;
   b) a first botanical compound of inhibiting the adherence of the organism to the surface of skin or mucosa by at least about 50%, wherein the first botanical compound is Goldenseal;

c) a second botanical compound capable of inhibiting the growth of the organism on or around the skin surface, wherein the second botanical compound has an IC50 value of about 5% or less for the organism and is Canadian Willowherb, and wherein at least one of the first botanical compound and second botanical compound is encapsulated; and wherein the organism is selected from the group consisting of *Candida albicans, Proteus mirabilis, Pseudomonas aeruginosa*, and *Staphylococcus epidermidis*.

13. The product as set forth in claim 7 wherein the first botanical compound and second botanical compound are encapsulated.

* * * * *